United States Patent
Weng et al.

(10) Patent No.: US 9,604,894 B2
(45) Date of Patent: Mar. 28, 2017

(54) COMPOUNDS FROM ANTRODIA CAMPHORATE AND THEIR USE IN TREATMENT OF DIABETES MELLITUS

(71) Applicant: National Dong Hwa University, Hualien (TW)

(72) Inventors: Ching-Feng Weng, Taipei (TW); Chin-piao Chen, Taipei (TW); Sulake Rohidas Shivaji, Maharashtra (IN); Chia-Yu Hsu, Taipei (TW)

(73) Assignee: National Dong Hwa University, Hualien (TW)

( * ) Notice: Subject to any disclaimer, the term of this patent is extended or adjusted under 35 U.S.C. 154(b) by 0 days.

(21) Appl. No.: 14/161,213

(22) Filed: Jan. 22, 2014

(65) Prior Publication Data
US 2015/0203430 A1   Jul. 23, 2015

(51) Int. Cl.
| | |
|---|---|
| *A61K 31/122* | (2006.01) |
| *C07C 49/753* | (2006.01) |
| *A61K 38/28* | (2006.01) |
| *C07C 45/65* | (2006.01) |
| *C07C 45/29* | (2006.01) |

(52) U.S. Cl.
CPC .......... *C07C 49/753* (2013.01); *A61K 31/122* (2013.01); *A61K 38/28* (2013.01); *C07C 45/294* (2013.01); *C07C 45/65* (2013.01); *C07C 2101/14* (2013.01); *C07C 2101/16* (2013.01)

(58) Field of Classification Search
None
See application file for complete search history.

(56) References Cited

U.S. PATENT DOCUMENTS

2013/0172424 A1* 7/2013 Liu et al. ............... 514/690

FOREIGN PATENT DOCUMENTS

CA   2837563 A1 * 12/2012

OTHER PUBLICATIONS

Chiang, Po-Cheng et al; "Antroquinonol displays anticancer potential against human hepatocellular carcinoma cells: A crucial role of AMPK and mTOR pathways." Biochem. Pharmacol. (2010) 79 p. 162-171.*
Kumar, K. J. Senthil et al, "Antroqunonol from ethanolic extract of mycelium of antrodia cinnamomea protects hepatic cells from ethanol induced oxidative stress through nrf-2 activation." J. Ethnopharmacology (2011) 136 p. 168-177.*
Xue, Mingzhan et al, "Activation of nf-e2-related factor-2 reverses biochemical dysfunction of endothelial cells induced by hyperglycemia linked to vascular disease." Diabetes (2008) 57 p. 2809-2817.*
Joslin, Elliott P., "The treatment of idabetes mellitus." Can. Med. Assoc. J. (1924) 14(9) 808-811.*
May 5, 2008 press release from Biotech East, http://www.biotecheast.com/index.php?module=htmlpages&func=display&pid=119.*
Chen, Kuan-Chou et al, "Unique formosan mushroom antrodia camphorata differentially inhibits androgen responsive Incap and inedpendent pc-3 prostate cancer cells." Nut. Canc. (2007) 57(1) p. 111-121.*
March, Jerry "Advanced organic chemistry" ISBN 0-471-60180-2 (1992) p. 797-803.*

* cited by examiner

*Primary Examiner* — Fred Reynolds
(74) *Attorney, Agent, or Firm* — Foxrothschild LLP

(57) ABSTRACT

The present invention relates to a method or composition for treating diabetes mellitus, comprising administering a subject with a pharmaceutical composition comprising a therapeutically effective amount of an active compound from *Antrodia camphorate*, such as antroquinonols, and a pharmaceutically acceptable carrier. In addition, the prevent invention provides a new process for the total synthesis of antroquinonol. Also provided are the new compounds produced during the process for preparing of antroquinonol.

4 Claims, 6 Drawing Sheets

COMPOUNDS FROM ANTRODIA CAMPHORATE AND THEIR USE IN TREATMENT OF DIABETES MELLITUS

FIELD OF THE INVENTION

The present invention relates to a method and composition for treating diabetes mellitus. In particular, the present invention relates to a method and composition for treating diabetes mellitus using some specific compounds from *Antrodia camphorate*.

BACKGROUND OF THE INVENTION

Type 2 diabetes mellitus (T2DM) is the most common chronic diseases and high prevalence in worldwide. It was suggested in the recent long-term mega trials that intensive glycemic control was used to reduce the aggravation of insulin resistance, particularly in T2DM, and the risk of cardiovascular disease (CVD) (Avogaro, "Treating diabetes today with gliclazide MR: a matter of numbers." *Diabetes, obesity & metabolism* 14 Suppl 1: 14-19, 2012). Accordingly, it is more desirable to develop the agents for glycemic control, than insulin analogous. For instance, sitagliptin that provides the effect for glycemic control has been developed as an agent for treating T2DM, which is a highly selective dipeptidyl peptidase-4 inhibitor (Goldstein et al., "Effect of initial combination therapy with sitagliptin, a dipeptidyl peptidase-4 inhibitor, and metformin on glycemic control in patients with type 2 diabetes." *Diabetes Care* 30(8): 1979-1987, 2007). Furthermore, metformin was reported to be effective for glycemic control by activating the AMP-activated protein kinase (AMPK) (Riddle, "Oral pharmacologic management of type 2 diabetes." *American Family Physician* 60(9): 2613-2620, 1999; Zhou et al., "Role of AMP-activated protein kinase in mechanism of metformin action." *Journal of Clinical Investigation* 108(8): 1167-1174, 2001; Fryer et al., "The Anti-diabetic drugs rosiglitazone and metformin stimulate AMP-activated protein kinase through distinct signaling pathways." *Journal of Biological Chemistry* 277(28): 25226-25232, 2002; Leverve et al., "Mitochondrial metabolism and type-2 diabetes: a specific target of metformin." *Diabetes and Metabolism* 29(4 Pt 2): 6S88-94, 2003). Sitagliptin and metformin are widely used as first-line drugs for treatment of T2DM to reduce blood sugar levels through different mechanisms. In the previous clinical trials, the efficacy of initial combination therapy with sitagliptin and metformin was confirmed in patients with T2DM.

Some Chinese herbs have been reported to be potential to reduce blood glucose level (Lee et al., "Berberine, a natural plant product, activates AMP-activated protein kinase with beneficial metabolic effects in diabetic and insulin-resistant states." *Diabetes* 55(8): 2256-2264, 2006; Shi et al., "Tiliroside-derivatives enhance GLUT4 translocation via AMPK in muscle cells." *Diabetes research and clinical practice* 92(2): e41-46, 2011). *Cinnamomum kanehirai* is one of species Lauraceae only from Taiwan (Wu et al., "*Antrodia camphorata* ("niu-chang-chih"), new combination of a medicinal fungus in Taiwan." *BOTANICAL BULLETIN-ACADEMIA SINICA TAIPEI* 38: 273-276, 1997). *Antrodia camphorate* is a parasitic fungal on the inner cavity of *C. kanehirae* (Geethangili et al., "Review of Pharmacological Effects of *Antrodia camphorata* and Its Bioactive Compounds." *Evidence-Based Complementary and Alternative Medicine* 2011: 212641, 2011).

It is still desirable to develop new drugs for treating T2DM and new process for chemical synthesis thereof.

BRIEF SUMMARY OF THE INVENTION

It is unexpectedly found in the invention that some compounds isolated from *Antrodia camphorate* are effective in treating diabetes mellitus, particularly T2DM.

In one aspect, the invention provides a method for treating diabetes mellitus in a subject comprising administering the subject with a pharmaceutical composition comprising a pharmaceutically acceptable carrier and a therapeutically effective amount of a compound having the general formula (I):

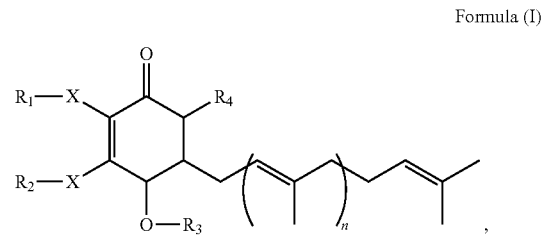

Formula (I)

wherein X and Y are the same or different, independently oxygen or sulfur, each of $R_1$, $R_2$, $R_3$ and $R_4$ is a hydrogen atom, methyl or $(CH_2)_m$—$CH_3$, m is an integer of 1-12, and n is an integer of 1-12.

In one embodiment of the invention, the compound having the general formula (I) can be isolated from *Antrodia camphorate*. One example of the invention is antroquinonol, particularly (+) or (−)-antroquinonol.

In one embodiment of the invention, the antroquinonol is effective for inhibiting Dipeptidyl peptidase-4 (DPP4) activity and enhancing AMP-activated protein kinase (AMPK) activation.

In a further aspect, the invention provides a new process for preparation of antroquinonol comprising the steps of asymmetric addition of diethyl zinc, Claisen rearrangement, ring-closing metathesis, and lactonization.

In a yet aspect, the invention provides new compound, (−)-antroquinonol having the general formula (IV):

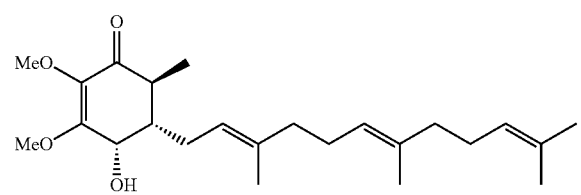

Formula (IV)

wherein Me is methyl.

In one embodiment of the invention, the (−)-antroquinonol is non-toxic.

In a further yet aspect, the invention provides some new compounds during the process for preparation of antroquinonol, including:

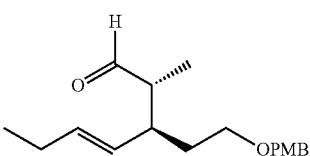

wherein PMB is p-methoxybenzyl;

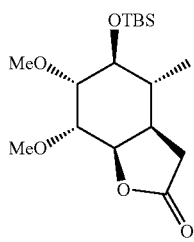

wherein Me is methyl, and TBS is tert-butyldimethylsilyl; and

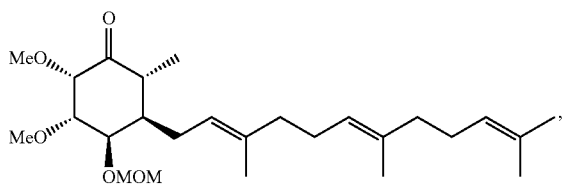

wherein Me is methyl, and MOM is methoxymethyl.

In a further yet further aspect, the invention provides a pharmaceutical composition in combination of the compound of general formula (I). One example of the invention is the pharmaceutical composition in combination of antroquinonol, particularly (+) or (−)-antroquinonol.

It is believed that a person of ordinary knowledge in the art where the present invention belongs can utilize the present invention to its broadest scope based on the descriptions herein with no need of further illustration. Therefore, the following descriptions should be understood as of demonstrative purpose instead of limitative in any way to the scope of the present invention.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 3(A) provides the results of the AKT Thr308 phosphorylation induced by insulin, metformin (Met) and antroquinonol (Ant); wherein the differentiated C2C12 cells were incubated with 100 nM of insulin, 16 mM of metformin (Met), or 25 μM of antroquinonol (Ant) at 37° C. for 30 min, and then the cell lysates were separated by SDS-PAGE and blotted for phospho-AKT Thr308; wherein the data were expressed as means with standard errors of mean (mean±SEM), and different letters represent the significant differences (p<0.05) among the various treatments.

FIG. 3(B) provides the results of AMPK Thr172 phosphorylation induced by insulin, metformin (Met) and antroquinonol (Ant); wherein the differentiated C2C12 cells were incubated with 100 nM of insulin, 16 mM of metformin (Met), or 25 μM of antroquinonol (Ant) at 37° C. for 30 min, and then the cell lysates were separated by SDS-PAGE and blotted for phospho-AMPK Thr172; wherein the data were expressed as means with standard errors of mean (mean±SEM), and different letters represent the significant differences (p<0.05) among the various treatments.

FIG. 5(A) shows the effects of insulin (Ins), metformin (Met) and antroquinonol (Ant) on GLUT4 translocation; wherein the C2C12 cells were differentiated, and treated with 185 μM insulin (Ins), 16 mM metformin (Met), and 50 μM, 100 μM, and 150 μM of antroquinonol (Ant) for 55 min (n=5 in each group); wherein the data were expressed as means with standard errors of mean (mean±SEM), and different letters represent the significant differences (p<0.05) among the various treatments.

FIG. 5(B) shows the ratios to the control on GLUT4 translocation; wherein the C2C12 cells were differentiated, and treated with 185 μM of insulin (Ins), 100 μM of antroquinonol, and insulin plus 100 μM of antroquinonol for 40 min (n=5 in each group), and the data were expressed as means with standard errors of mean (mean±SEM), and different letters represent the significant differences (p<0.05) among the various treatments.

Figure 7A:
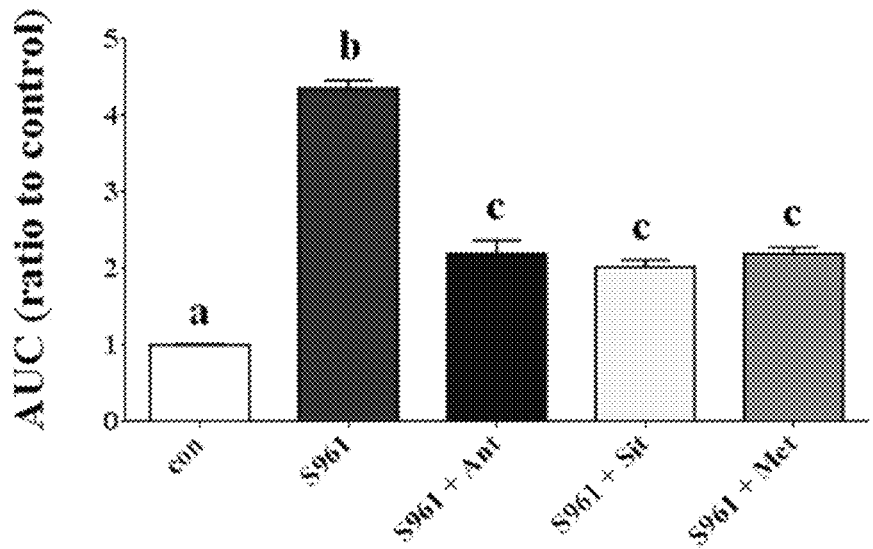
Figure 7B:
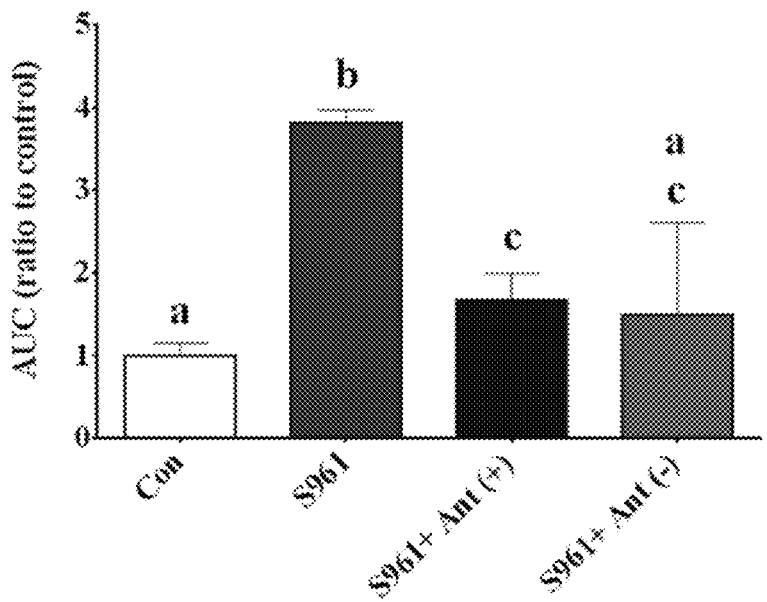

FIGS. 7(A) and 7(B) show the hypoglycemic efficacy of antroquinonol in the condition of insulin resistance through the oral glucose tolerance test (OGTT):

FIG. 7(A) shows the AUC (ratio to the control) of antroquinonol (Ant) through the oral glucose tolerance test (OGTT); wherein the blood glucose change presented by AUC (area under curve) of mice treated with 5961 (an antagonist for insulin receptor, used to mimic DM) at 40 nmol/kg Body weight (Bwt) followed by Metformin (Met) at 100 mg/kg Bwt as positive control, antroquinonol (Ant) at 50 mg/kg Bwt, and Sitagliptin (Sit) at 10 mg/kg Bwt; then all mice were treated with D-glucose at 2 g/kg Bwt (n=5 in each group); wherein the data were expressed as means with standard errors of mean (mean±SEM), and different letters represent significant differences (p<0.05) among various treatments.

FIG. 7(B) shows the efficacy of (+)-antroquinonol (Ant (+)) and (−)-antroquinonol (Ant(−)) in the condition of insulin resistance through the oral glucose tolerance test (OGTT); wherein the blood glucose change presented by AUC (area under curve) of the mice treated with 5961 at 50 nmol/kg Bwt followed by an oral administration (p.o.) of (+)-antroquinonol (Ant(+)) or (−)-antroquinonol (Ant(−)) at 50 mg/kg Bwt (dissolved in PEG and EtOH), then all mice were treated with D-glucose at 2 g/kg Bwt and D-glucose (2 g/kg Bwt), and OGTT test was performed; wherein the data were expressed as means with standard errors of mean (mean±SEM), and different letters represent significant differences (p<0.05) among the various treatments.

Figure 8:
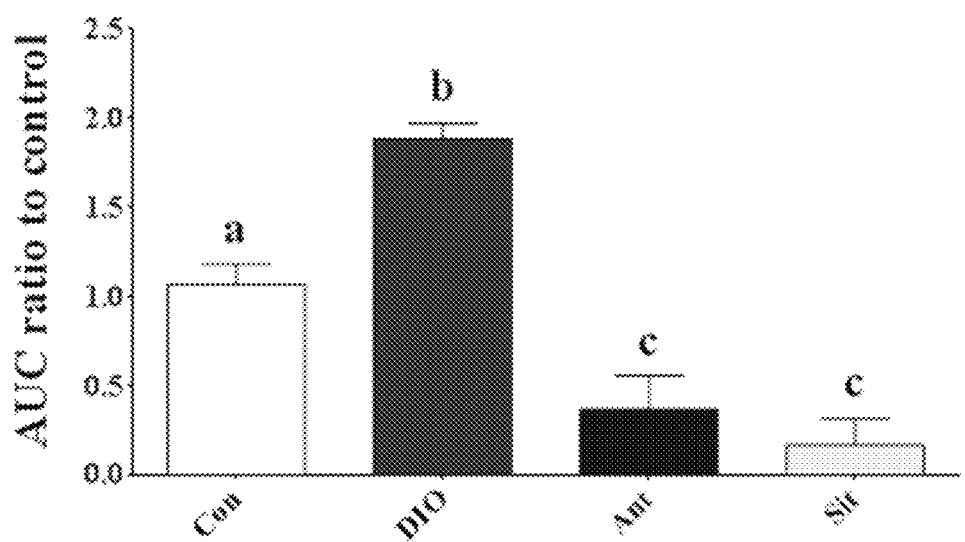

FIG. 8 shows the effect of antroquinonol in reducing blood glucose in DIO mice after a short term treatment; wherein the DIO mice were treated with antroquinonol (Ant) at 25 mg/kg Bwt or Sitagliptin (Sit) at 20 mg/kg Bwt, and the oral glucose tolerance test was performed to measure the changes of blood glucose (in terms of AUC) in the mice (n=5 in each group); wherein the data are expressed as means with standard errors of mean (mean±SEM), and different letters represent significant differences (p<0.05) among the various treatments.

Figure 9:
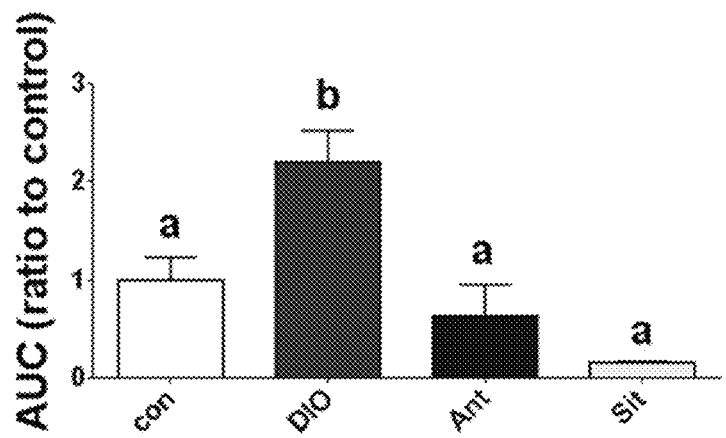

FIG. 9 shows the effect of antroquinonol in reducing blood glucose in DIO mice after a long term treatment; wherein the DIO mice were treated with antroquinonol (Ant) at 25 mg/kg Bwt or Sitagliptin (Sit) at 10 mg/kg Bwt for 4 weeks (n=5 in each group), and then the oral glucose tolerance test was performed to measure the changes of blood glucose (in terms of AUC) in the mice (n=5 in each group); the data were expressed as means with standard errors of mean (mean±SEM), and different letters represent significant differences (p<0.05) among various treatments.

DETAILED DESCRIPTION OF THE INVENTION

Unless otherwise defined, all technical and scientific terms used herein have the same meaning as commonly understood by one of ordinary skill in the art to which this invention pertains. In the case of conflict, the present document, including definitions will be controlled.

As used herein, the singular forms "a", "an", and "the" include plural referents unless the context clearly dictates otherwise. Thus, for example, reference to "a sample" includes a plurality of such samples and equivalents thereof known to those skilled in the art.

The following abbreviations are used herein to designate the compounds of the invention: methyl ("ME"), p-methoxybenzyl ("PMB"), tert-butyldimethylsilyl ("TBS") and methoxymethyl ("MOM").

As used herein, the term "subject" refers to a human or a mammal, such as a patient, a companion animal (e.g., dog, cat, and the like), a farm animal (e.g., cow, sheep, pig, horse, and the like) or a laboratory animal (e.g., rat, mouse, rabbit, and the like).

It is first discovered in the present invention that antroquinonols have effects in inhibiting Dipeptidyl peptidase-4 (DPP4) activity and/or in enhancing AMP-activated protein kinase (AMPK) activation. It is evidenced in the present invention that antroquinonols provides similar or better effects than the drugs for treating diabetes mellitus, particularly type 2 diabetes mellitus (T2DM), by enhancing AMPK activation like the first line drug, metformin, and/or by inhibiting DPP4 activity like Sitagliptin. Accordingly, the present invention provides a new method/pharmaceutical composition for treatment of diabetes mellitus, particularly T2DM, improvement of glucose uptake, and glycemic control in the hyperglycemic mice (DM mice), particularly those with insulin resistance. In addition, it is also confirmed that antroquinonols provide synergistic effects in combination of and insulin.

According to the invention, the method for treating diabetes mellitus in a subject comprising administering the subject with a pharmaceutical composition comprising a pharmaceutically acceptable carrier and a therapeutically effective amount of a compound having the general formula (I):

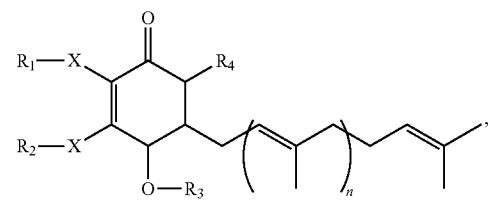

Formula (I)

wherein X and Y are the same or different, independently oxygen or sulfur, each of $R_1$, $R_2$, $R_3$ and $R_4$ is a hydrogen atom, methyl or $(CH_2)_m$—$CH_3$, m is an integer of 1-12, and n is an integer of 1-12.

The compound having the general formula (I) can be isolated from *Antrodia camphorate*, using commonly known methods or standard methodologies to persons with ordinary skill in the art.

One example of the compound is antroquinonol, which has a general formula (II) below:

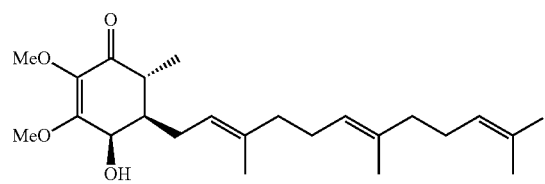

Formula (II)

Antroquinonol is a well-known compound only found in fermentation of *A. camphorate* (Kuo et al., Novel compounds from *antrodia camphorata*, US20100130584A1). In the conventional methods, the purification of antroquinonol from ferments costs highly but gets low recovery. Antroquinonol includes (+) and (−)-antroquinonol, however (−)-antroquinonol has not been isolated before the present invention. The (+)-antroquinonol has the general formula (III):

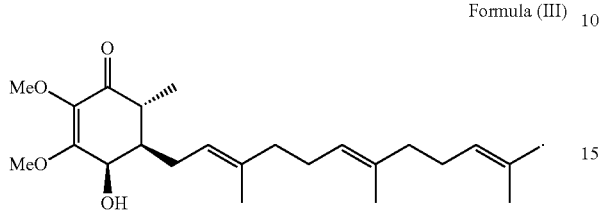

Formula (III)

On the other hand, the (−)-antroquinonol has the general formula (IV), which is first isolated in the present invention:

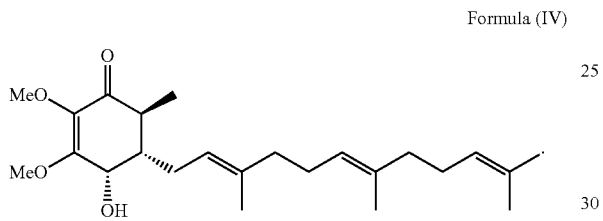

Formula (IV)

Figure 1:
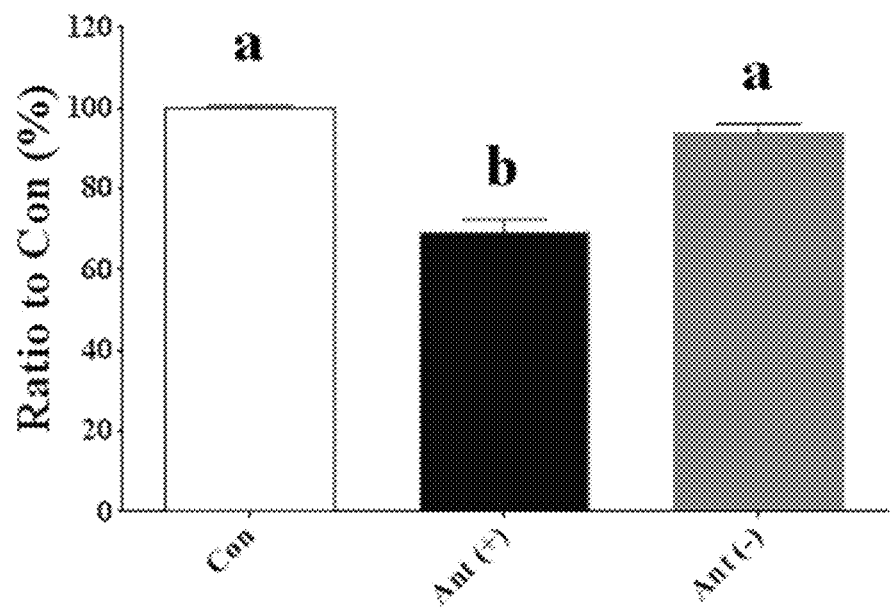
FIG. 1 shows the result of MTT assay for (+) and (−)-antroquinonol (represented by "Ant (+)" and "Ant (−)" respectively) as compared with a control (represented by "Con"); wherein LNCaP cells were incubated at 37° C. in 5% $CO_2$ overnight, and treated with 10 μM (+)-antroquinonol or (−)-antroquinonol for 48 h and further incubated for 4 h followed by an MTT assay, the OD value per well was measured at 570 nm; wherein the data were expressed as means with standard deviations (mean±SD), and different letters represent the significant differences (p<0.05) among the various treatments.

In the example of the invention, the cell viability of cells treated with (−)-antroquinonol was similar to that of the control (Con) as shown in FIG. 1, indicating that (−)-antroquinonol is non-toxic.

The invention also provided a new process for the total synthesis of antroquinonol. The process for preparation of antroquinonol comprises the steps of asymmetric addition of diethyl zinc, Claisen rearrangement, ring-closing metathesis, and lactonization.

The process is an enantioselective synthesis involving an iridium-catalyzed olefin isomerization-Claisen rearrangement (ICR), a lactonization, and a Grubbs metathesis reaction for the establishment of three stereogenic centers. The requisite α,β-unsaturation was achieved using a selenylation/oxidation protocol.

The total synthesis of (+)-antroquinonol was performed according to the scheme below:

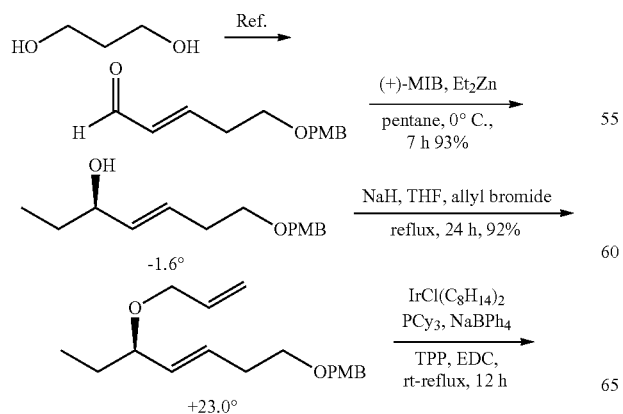

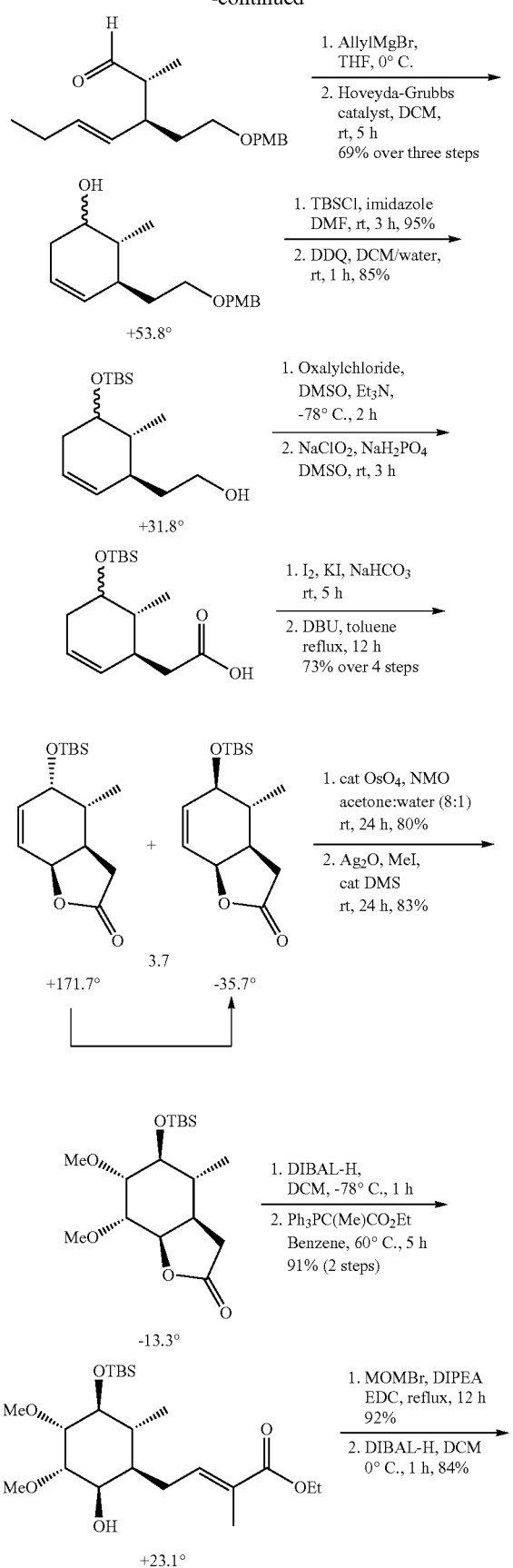

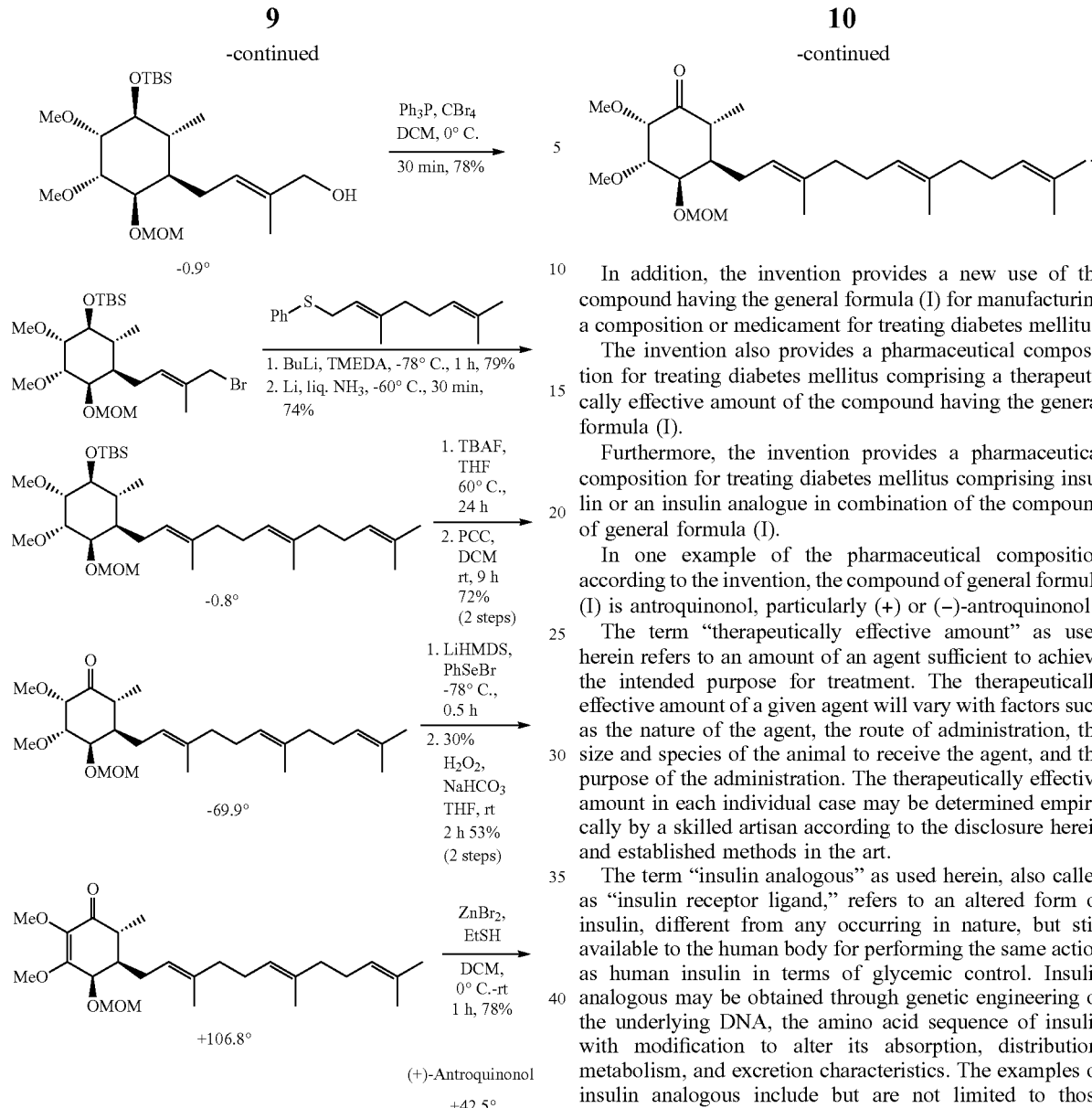

During the above described process for preparation of antroquinonol, some new compounds are found and provided in the invention, including:

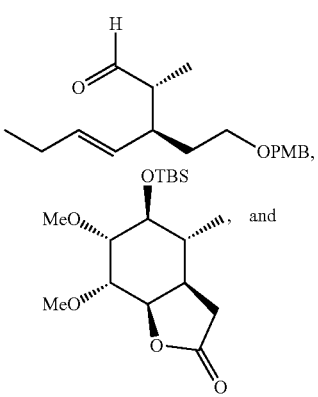

In addition, the invention provides a new use of the compound having the general formula (I) for manufacturing a composition or medicament for treating diabetes mellitus.

The invention also provides a pharmaceutical composition for treating diabetes mellitus comprising a therapeutically effective amount of the compound having the general formula (I).

Furthermore, the invention provides a pharmaceutical composition for treating diabetes mellitus comprising insulin or an insulin analogue in combination of the compound of general formula (I).

In one example of the pharmaceutical composition according to the invention, the compound of general formula (I) is antroquinonol, particularly (+) or (−)-antroquinonol.

The term "therapeutically effective amount" as used herein refers to an amount of an agent sufficient to achieve the intended purpose for treatment. The therapeutically effective amount of a given agent will vary with factors such as the nature of the agent, the route of administration, the size and species of the animal to receive the agent, and the purpose of the administration. The therapeutically effective amount in each individual case may be determined empirically by a skilled artisan according to the disclosure herein and established methods in the art.

The term "insulin analogous" as used herein, also called as "insulin receptor ligand," refers to an altered form of insulin, different from any occurring in nature, but still available to the human body for performing the same action as human insulin in terms of glycemic control. Insulin analogous may be obtained through genetic engineering of the underlying DNA, the amino acid sequence of insulin with modification to alter its absorption, distribution, metabolism, and excretion characteristics. The examples of insulin analogous include but are not limited to those illustrated in Hirsch, "Insulin analogues", New England J Med 2005; 352:174-183, 2005.

The pharmaceutical composition of the invention may be administered in any route that is appropriate, including but not limited to parenteral or oral administration. The pharmaceutical compositions for parenteral administration include solutions, suspensions, emulsions, and solid injectable compositions that are dissolved or suspended in a solvent immediately before use. The injections may be prepared by dissolving, suspending or emulsifying one or more of the active ingredients in a diluent. Examples of said diluents are distilled water for injection, physiological saline, vegetable oil, alcohol, and a combination thereof. Further, the injections may contain stabilizers, solubilizers, suspending agents, emulsifiers, soothing agents, buffers, preservatives, etc. The injections are sterilized in the final formulation step or prepared by sterile procedure.

According to the invention, the composition may be administered through oral route, wherein the composition may be in a solid or liquid form. The solid compositions include tablets, pills, capsules, dispersible powders, granules, and the like. The oral compositions also include gargles which are to be stuck to oral cavity and sublingual tablets.

The capsules include hard capsules and soft capsules. In such solid compositions for oral use, one or more of the active compound(s) may be admixed solely or with diluents, binders, disintegrators, lubricants, stabilizers, solubilizers, and then formulated into a preparation in a conventional manner. When necessary, such preparations may be coated with a coating agent, or they may be coated with two or more coating layers. On the other hand, the liquid compositions for oral administration include pharmaceutically acceptable aqueous solutions, suspensions, emulsions, syrups, elixirs, and the like. In such compositions, one or more of the active compound(s) may be dissolved, suspended or emulsified in a commonly used diluent (such as purified water, ethanol or a mixture thereof, etc.). Besides such diluents, said compositions may also contain wetting agents, suspending agents, emulsifiers, sweetening agents, flavoring agents, perfumes, preservatives and buffers and the like.

The specific example below is to be construed as merely illustrative, and not limitative of the remainder of the disclosure in any way whatsoever. Without further elaboration, it is believed that one skilled in the art can, based on the description herein, utilize the present invention to its fullest extent.

EXAMPLES

Example 1 Preparation of Antroquinonol

The total synthesis of antroquinonol is performed by an enantioselective synthesis, involving an iridium-catalyzed olefin isomerization-Claisen rearrangement (ICR), a lactonization, and a Grubbs metathesis reaction for the establishment of three stereogenic centers; wherein the critical $\alpha,\beta$-unsaturation was achieved by using a selenylation/oxidation protocol.

1.1 Scheme for (+)-Antroquinonol

The total synthesis of (+)-antroquinonol was performed according to the scheme below:

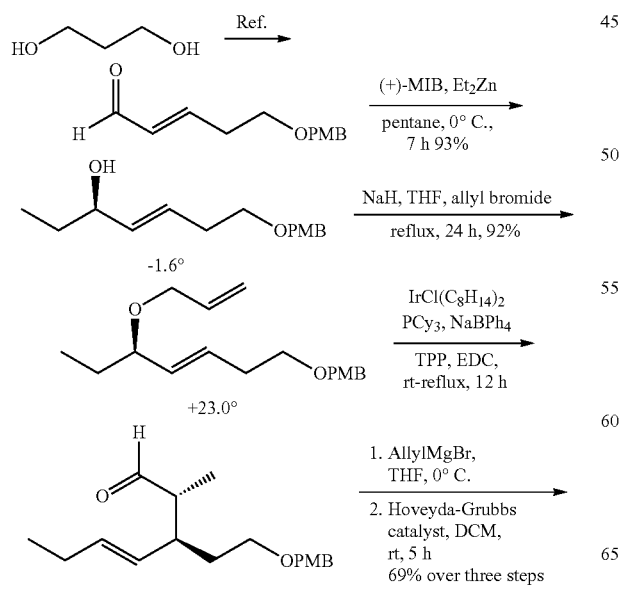

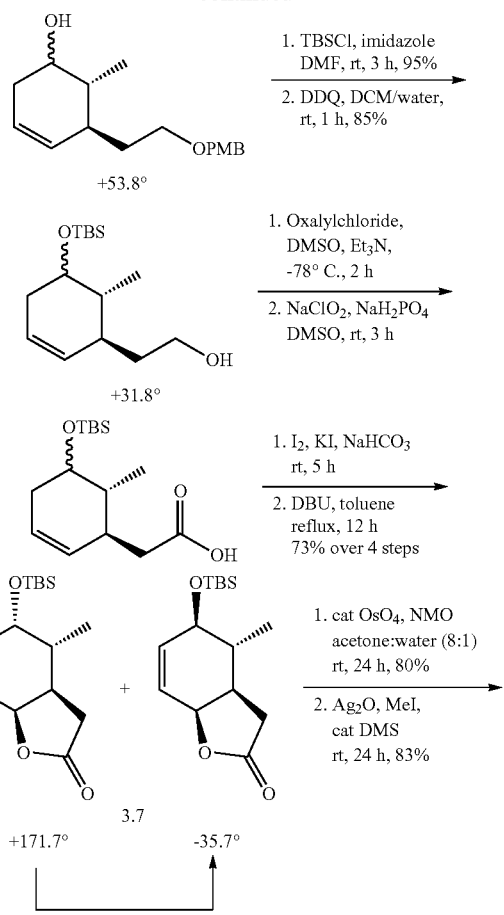

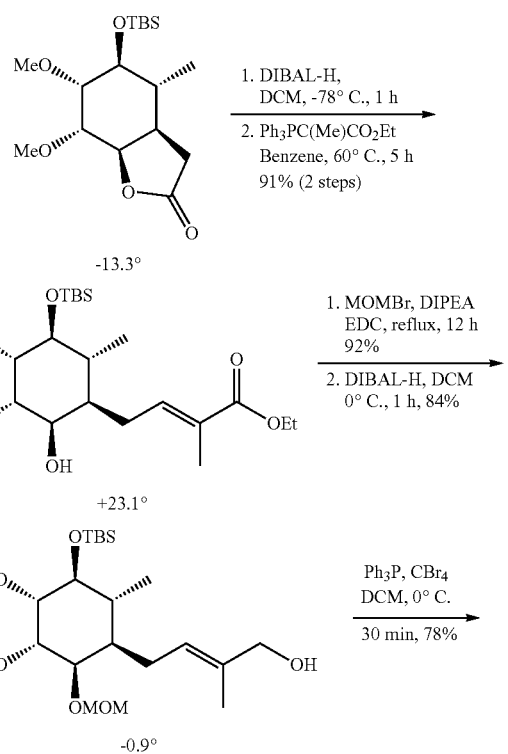

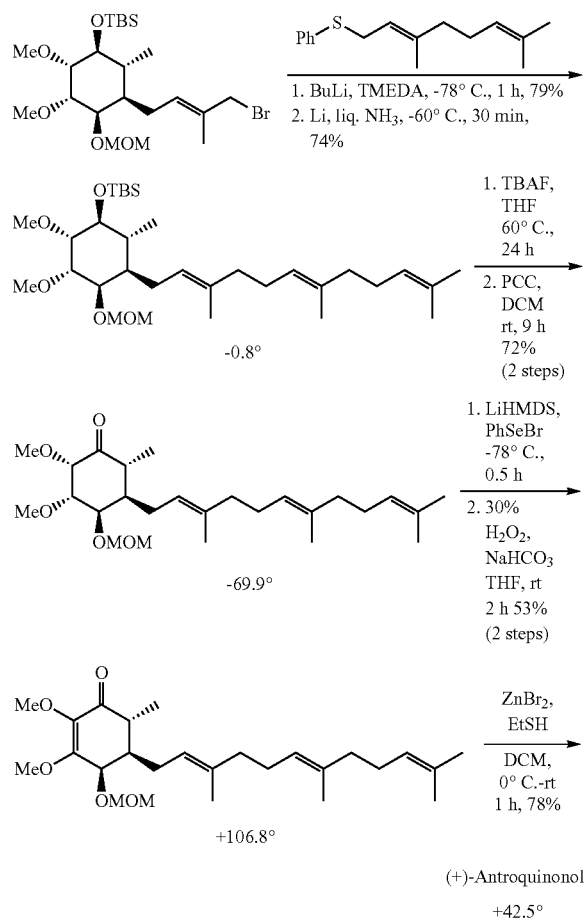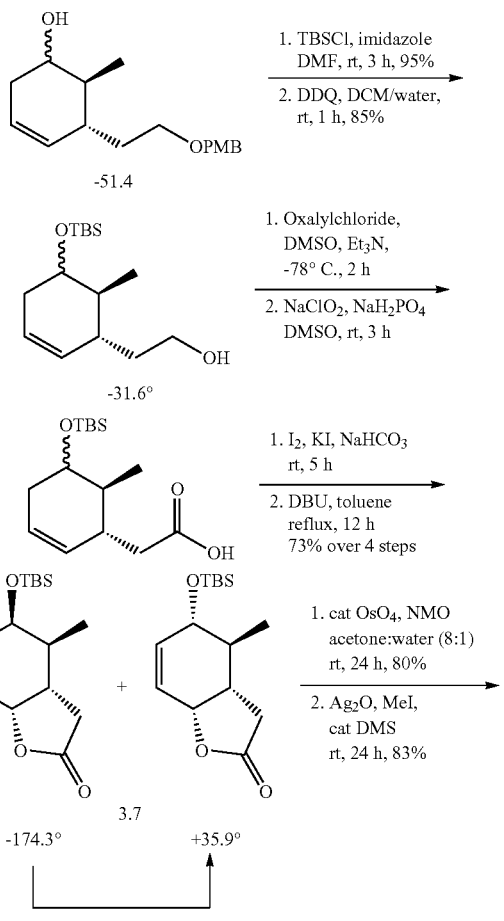
1.2 Scheme for (−)-Antroquinonol
The total synthesis of (−)-antroquinonol was performed according to the scheme below:
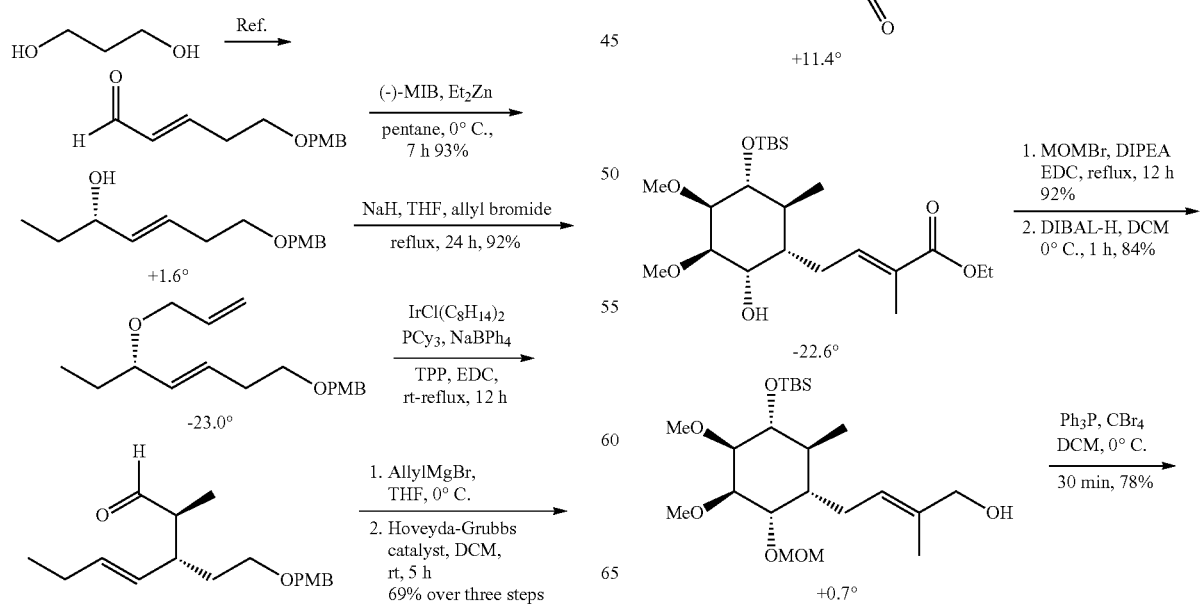

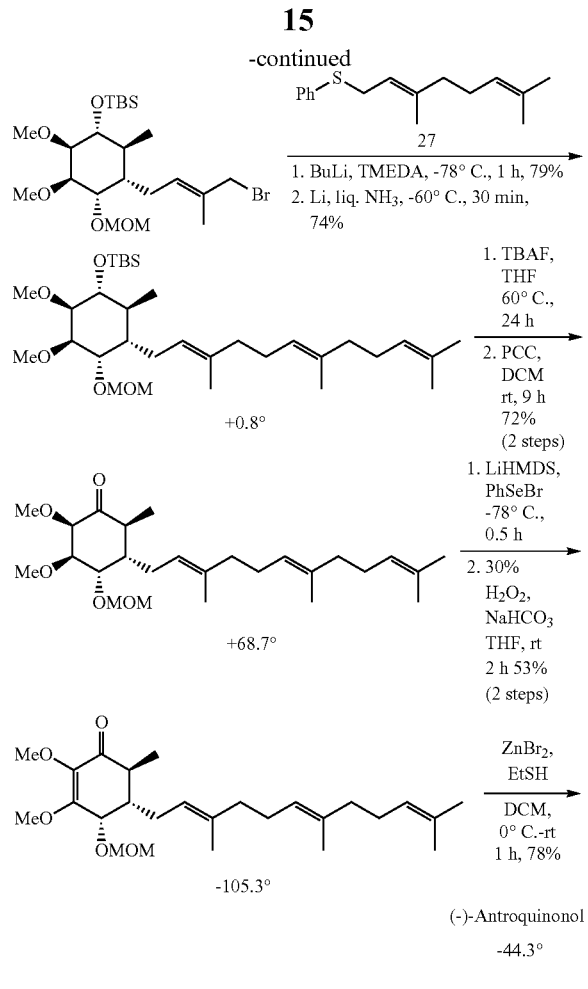

1.3 Characterization

The spectral data of antroquinonol were given as follows:

$[\alpha]_D^{25}$: +42.5° (c=1.20 in CHCl$_3$). IR (film): 3435, 2926, 1659.3, 1622, 1451, 1358, 1240, 1141, 1017, 944, 832, 749 cm$^{-1}$. $^1$H-NMR (400 MHz, CDCl$_3$): δ 5.16 (m, 1H), 5.08 (m, 2H), 4.34 (d, J=3.24 Hz, 1H), 4.06 (s, 3H), 3.66 (s, 3H), 2.52 (m, 1H), 2.23 (dd, J=7.48 Hz, J=7.44 Hz, 2H), 1.97-2.09 (m, 9H), 1.75 (m, 1H), 1.67 (s, 3H), 1.66 (s, 3H), 1.60 (s, 6H), 1.17 (d, J=6.92 Hz, 3H). $^{13}$C-NMR (100.6 MHz, CDCl$_3$): δ 197.12, 160.49, 138.03, 135.92, 135.34, 131.31, 124.31, 123.85, 120.99, 67.91, 60.58, 59.19, 43.40, 40.27, 39.81, 39.71, 27.00, 26.74, 26.45, 25.69, 17.67, 16.12, 16.01, 12.31. HRMS-EI (m/z) [M]$^+$ calcd for C$_{26}$H$_{42}$O$_5$ 390.2770. found 390.2764.

1.4 Characterization of New Compounds

During the process for preparing antroquinonol, the following new compounds are found:

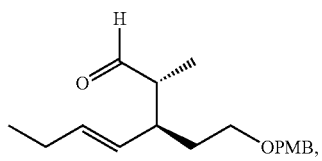

the spectral data are given as follows:

$^1$H-NMR (400 MHz, CDCl$_3$): δ 9.64 (d, J=2.20 Hz, 1H), 7.23 (m, 3H), 6.87 (d, J=8.60 Hz, 2H), 5.49 (m, 1H), 5.18 (m, 1H), 4.42 (d, J=11.52 Hz, 1H), 4.36 (d, J=11.52 Hz, 1H), 3.80 (s, 3H), 3.40 (m, 2H), 2.34 (m, 1H), 2.30 (m, 1H), 2.02 (m, 2H), 1.70 (m, 1H), 1.56 (m, 1H), 1.05 (d, J=5.72 Hz, 3H), 0.96 (t, J=4.08 Hz, 3H);

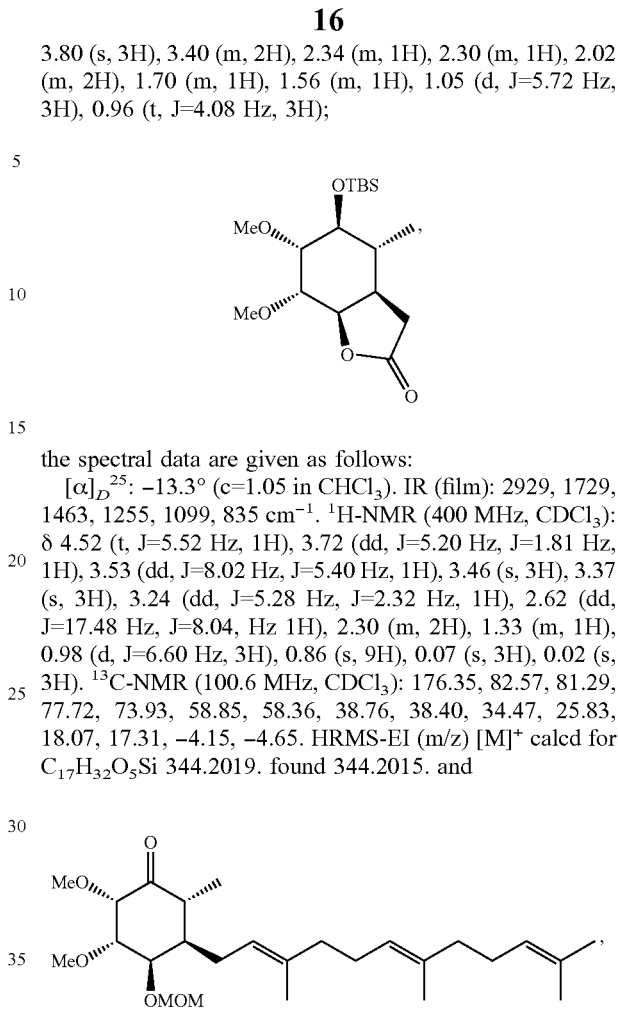

the spectral data are given as follows:

$[\alpha]_D^{25}$: −13.3° (c=1.05 in CHCl$_3$). IR (film): 2929, 1729, 1463, 1255, 1099, 835 cm$^{-1}$. $^1$H-NMR (400 MHz, CDCl$_3$): δ 4.52 (t, J=5.52 Hz, 1H), 3.72 (dd, J=5.20 Hz, J=1.81 Hz, 1H), 3.53 (dd, J=8.02 Hz, J=5.40 Hz, 1H), 3.46 (s, 3H), 3.37 (s, 3H), 3.24 (dd, J=5.28 Hz, J=2.32 Hz, 1H), 2.62 (dd, J=17.48 Hz, J=8.04, Hz 1H), 2.30 (m, 2H), 1.33 (m, 1H), 0.98 (d, J=6.60 Hz, 3H), 0.86 (s, 9H), 0.07 (s, 3H), 0.02 (s, 3H). $^{13}$C-NMR (100.6 MHz, CDCl$_3$): 176.35, 82.57, 81.29, 77.72, 73.93, 58.85, 58.36, 38.76, 38.40, 34.47, 25.83, 18.07, 17.31, −4.15, −4.65. HRMS-EI (m/z) [M]$^+$ calcd for C$_{17}$H$_{32}$O$_5$Si 344.2019. found 344.2015. and the spectral data are given as follows:

$[\alpha]_D^{25}$: −69.9° (c=1.15 in CHCl$_3$). IR (film): 2926, 1725, 1651, 1633, 1458, 1449, 1119, 1031 cm$^{-1}$. $^1$H-NMR (400 MHz, CDCl$_3$): δ 5.09 (m, 3H), 4.74 (d, J=6.84 Hz, 1H), 4.69 (d, J=6.84 Hz, 1H), 4.25 (d, J=2.64 Hz, 1H), 4.10 (t, J=3.48 Hz, 1H), 3.87 (t, J=3.08 Hz, 1H), 3.48 (s, 3H), 3.46 (s, 3H), 3.43 (s, 3H), 2.19 (m, 1H), 1.94-2.08 (m, 10H), 1.36 (s, 3H), 1.33 (s, 3H), 1.32 (s, 6H), 1.25 (m, 1H), 1.07 (d, J=6.52 Hz, 3H). $^{13}$C-NMR (100.6 MHz, CDCl$_3$): δ 207.87, 136.84, 135.23, 131.23, 124.28, 123.95, 122.07, 98.29, 83.96, 83.03, 76.25, 58.99, 58.53, 56.09, 44.46, 44.02, 39.75, 39.71, 27.25, 26.73, 26.57, 25.66, 17.64, 16.21, 15.97, 11.09. HRMS-EI (m/z) [M]$^+$ calcd for C$_{26}$H$_{44}$O$_5$ 436.3189. found 436.3184.

Example 2 Effects of (+)-Antroquinonol & (−)-Antroquinonol

2.1 MTT Assay

The 3-(4,5-dimethylthiazol-2-yl)-2,5-diphenyltetrazolium bromide (MTT, Invitrogen, USA) colorimetric based assay was performed to analyze the cell viability.

The LNCaP cells at a density of 7×10$^3$ cells per well were seeded in 96-well plates and were incubated for overnight at 37° C. in 5% CO$_2$. The cells were treated with 10 μM of (+)-antroquinonol or (−)-antroquinonol for 48 h, and then MTT solution was added per well, and the plates were incubated in MTT solution and further incubated for 4 h. The culture media was removed, and formazan was solubilized by adding 100 μL of DMSO per well and the OD value of each well was measured at 570 nm using a microplate reader (Thermo Labsystems, Opsys MR, Thermo fisher scientific, Waltham, Mass., USA).

As shown in FIG. 1, the cell viability of cells treated with (−)-antroquinonol was similar to that of the control (Con), suggesting that (−)-antroquinonol is non-toxic.

Example 3 Effect of Antroquinonol on the Inhibition of DPP4 Enzyme Activity

Dipeptidyl peptidase-4 (DPP4), also known as adenosine deaminase complexing protein 2 or CD26 (cluster of differentiation 26), is a drug for treating DM. DPP4 enzyme activity was measured by a DPPIV/CD26 Assay Kit (BML-AK498, Enzo, N.Y., USA). This assay is based on the cleavage of the p-nitroaniline (pNA) from the chromogenic substrate (H-Gly-Pro-pNA) to increase the absorbance at 405 nm. Firstly 50 μL of assay buffer (50 mM Glycine, pH 8.7, 1 mM EDTA) per will was added into the 96-well clear microplate, and then 20 μL of DPP4 enzyme (13 μU/μL), 20 μL of tested inhibitors, 100 μM of antroquinonol or known clinical drug sitagliptin, and finally 10 μL of pNA substrate were added to each well sequentially. After an incubation of reaction mixture at room temperature (RT) for 30 min, the absorbance of each sample was read at 405 nm by the ELISA plate reader (Thermo Labsystems, Opsys MR, Thermo fisher scientific).

Figure 2:
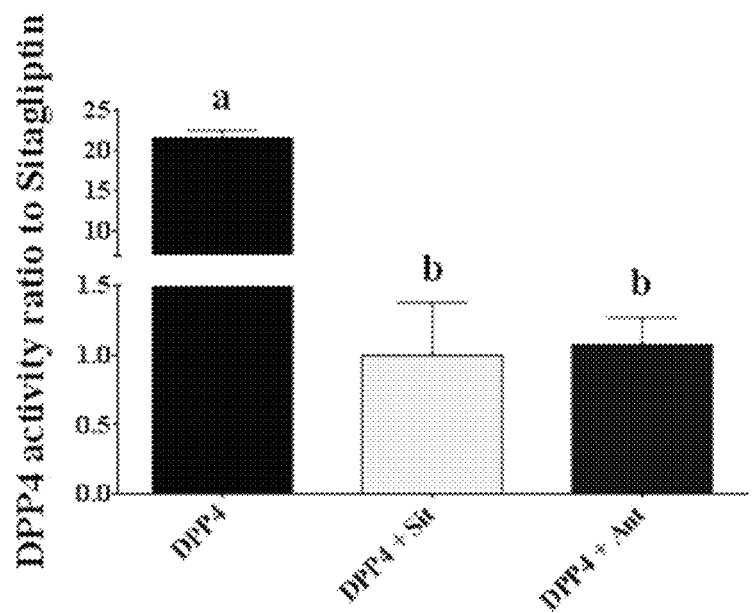
FIG. 2 shows the activity of antroquinonol in inhibiting the DPP4 activity; wherein the DPP4 activity levels of 100 μM antroquinonol (represented by "DPP4+Ant") and Sitagliptin (represented by "DPP4+Sit") as a comparison were determined by ELISA (DPP4/CD26 Assay Kit, BML-AK498) respectively; wherein the data were expressed as means with standard deviations (mean±SD), and different letters represent the significant differences (p<0.05) among the various treatments.

The activity of DPP4 of 100 μM antroquinonol (Ant) was compared with a known clinical drug, Sitagliptin (Sit). As shown in FIG. 2, antroquinonol (Ant) provided an effect in inhibition of DPP4 activity similar to that of sitagliptin (Sit), wherein the inhibitory rate (compared to the control without treatment) was up to 50%.

Example 4 Effect of Antroquinonol in Inducing AMPK Thr172 Phosphorylation and Insulin Signaling Pathway 4.1 Mouse Muscle Myoblast Cells (C2C12) Culture and Maintenance Mouse muscle myoblast cells (C2C12) were obtained from the Food Industry Research and Development Institute (FIRDI, Hsinchu, Taiwan). The cells were grown and maintained in Dulbecco's Modified Eagle's Medium containing high level of glucose (DMEM-high glucose; GIBCO, Carlsbad, Calif., USA) supplemented with 10% fetal bovine serum (FBS, GIBCO) and 1% penicillin streptomycin (GIBCO) in a cell culture incubator with 5% $CO_2$ at 37° C. Prior to experiment, the cells were seeded and cultured at a density of $8\times10^3$ cells per well in 96-well plates or $2.5\times10^5$ cells per well in 6-well plates. After the myoblasts achieved 80% confluence, the cells were incubated for 4 days in DMEM—high glucose supplemented with 1% FBS and 1% horse serum induced differentiation to myotubes.

4.2 Mouse Muscle Myoblast Cells (L6) Culture and Maintenance

Mouse muscle myoblast cells (L6) was a generous gift from Professor Hitoshi Ashida's Lab (Kobe University, Kobe, Japan). The cells were grown and maintained in α-minimal essential medium (α-MEM, 12000022, GIBCO) supplemented with 10% fetal bovine serum (FBS, GIBCO) and 1% penicillin streptomycin (GIBCO) in a cell culture incubator with 5% $CO_2$ at 37° C. Prior to experiments, the cells were seeded and cultured at a density of $8\times10^3$ cells per well in 96-well plates or $2.5\times10^5$ cells per well in 6-well plates. After the myoblasts achieved 80% confluence, the cells were incubated for 5 days in α-MEM supplemented with 2% FBS induced differentiation to myotubes.

4.3 Rat Pancreas Tumor Cells Culture and Maintenance

Rat pancreas tumor cells (AR42J) were obtained from the Food Industry Research and Development Institute (FIRDI, Hsinchu, Taiwan). The cells were grown and maintained in DMEM (GIBCO) supplemented with 20% fetal bovine serum (FBS, GIBCO) and 1% penicillin streptomycin (GIBCO) and 2 mM of L-glutamin in a cell culture incubator with 5% $CO_2$ at 37° C. Prior to the experiments, the cells were seeded and cultured for 16-24 h.

4.4 Western Blot

After treatments, the cells were collected and washed twice in cold KRH buffer (containing 50 mM HEPES, 137 mM NaCl, 4.8 mM KCl, 1.85 mM $CaCl_2$, 1.3 mM $MgSO_4$), and then lysed in ice-cold RIPA buffer (containing 50 mM Tris-HCl, pH 8.0, 150 mM NaCl, 5 mM NaF, 1% NP40, 1 mM sodium orthovanadate, 0.5% sodium deoxycholate, 0.1% sodium dodecyl sulphate (SDS), protease inhibitors, and phosphatase inhibitors (DE-68305, Roche, Mannheim, Germany)) and incubated at 4° C. for 60 min. After centrifugation of the cells at 12,000×g at 4° C. for 30 min, the supernatant was kept and quantified by Bradford protein assay (Bio-Rad, Hercules, Calif., USA). Proteins were separated using sodium dodecyl sulphate polyacrylamide gel electrophoresis (SDS-PAGE) and subsequently transferred to PVDF (Perkin Elmer Life Sciences, Boston, Mass., USA) membrane. The blots were blocked with 5% non-fat milk in TBS/T (containing 20 mM Tris-Base, 137 mM NaCl at pH 7.4 and 0.05% Tween-20) at Room Temperature (RT) for 1 h and then incubated with the appropriate primary antibody at 4° C. overnight. After wash, the blots were incubated with horseradish peroxidise (HRP)-conjugated secondary antibody (General Electric, Little Chalfont, Buckinghamshire, UK) for 1 h. The signals were monitored using Western Lightning™ Plus-ECL (Perkin Elmer Life Sciences) and the PVDF membrane was exposed to Luminescent image analyzer (LAS)-3000 (Fujifilm, Minato, Tokyo, Japan). The acquired data were analyzed and compared the difference among various treatments.

4.5 Effects of Antroquinonol on Inducing AKT Thr308 and AMPK Thr172 Phosphorylation It is known that GLUT4 translocation requires insulin-dependent PI3K/AKT activation signaling pathway or insulin-independent AMPK activation pathway in skeletal muscle. Therefore, the activations of AKT and AMPK were determined to learn via which pathway antroquinonol induces the action to induce GLUT4 translocation, insulin-dependent pathway or insulin-independent pathway. In this test, metformin and insulin were respectively administrated to control glucose uptake by activating AMPK and insulin signaling as positive controls.

The C2C12 cells were fully differentiated in DMEM supplemented with 1% FBS and 1% horse serum for 4 days. The cells were washed twice with PBS containing 0.1% BSA and subsequently incubated in PBS containing 0.1% BSA, and treated with or without insulin, metformin (Met) and antroquinonol (Ant) for 30 min. The treated cells were collected and washed twice in KRH, then lysed in ice-cold RIPA buffer for 60 min. After centrifugation at 12,000×g at 4° C. for 30 min, the supernatant was kept at −80° C. until use.

The C2C12 cells were treated with 100 nM insulin, 16 mM of metformin (Met), and 25 μM of antroquinonol (Ant) at 37° C. for 30 min. Then, the cell lysates were separated by SDS-PAGE and blotted for phospho-AKT (Thr308) and phospho-AMPK (Thr172). The proteins levels including phospho-AMPK (Thr172), AMPKα, phosphor-AKT (Thr308), and AKT (Cell Signalling, Boston, Mass., USA) were detected and evaluated by Western blot with primary antibody.

Figure 3A:
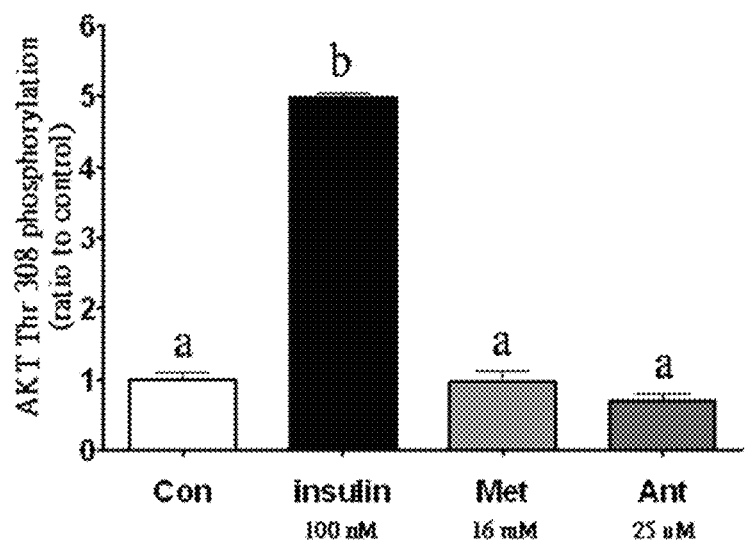
FIGS. 3(A) and 3(B) show the effects of antroquinonol on AKT Thr308 and AMPK Thr172 phosphorylation.

As shown in FIG. 3(A), insulin induced insulin signaling pathway at the phosphorylation of AKT Thr308 but not for metformin and antroquinonol.

Figure 3B:
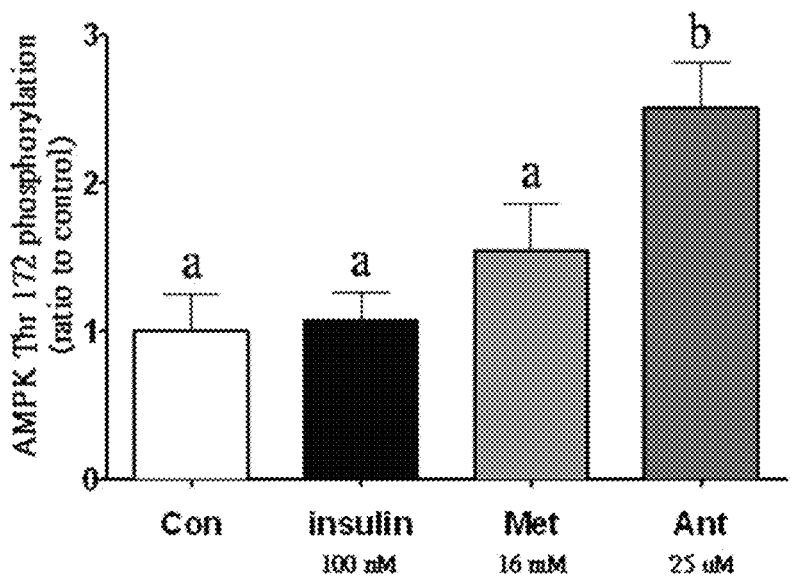

As shown in FIG. 3(B), metformin (Met) and antroquinonol (Ant) provided an effect in action to the phosphorylation of AMPK Thr172 in mouse myoblast C2C12 cells; specifically, antroquinonol (Ant) provided a significantly better efficacy on the phosphorylation of AMPK Thr172 than insulin and metformin. It was confirmed that antroquinonol alone possessed the in vitro ability to improve insulin-independent GLUT4 translocation via AMPK pathway.

4.7 Effect of Antroquinonol in Inhibiting DPP4 Potentiate Glucagon Like Peptide-1 Induced PKA Protein Level It is known that in pancreatic β cells, the inhibition of DPP4 helps incretin peptides binding to G protein-coupled receptors (GLP-1R and GIP-R), and the downstream pathway is mainly regulated by cAMP, when GLP-1 binds to GLP-1R to enhance cAMP, which leads the activation of PKA affect the subsequently $Ca^{2+}$ stimulates the insulin secretion.

The AR42J cells were treated with 1 nM glucagon-like peptide-1 (GLP-1, prospecbio, NJ, USA), 1 nM exendin-4 (Ex-4, Byetta, Eli Lilly, Indiana, USA), and antroquinonol for 48 h, and GAPDH as an internal control. The PKA protein expression levels were determined by Western blot.

Figure 4:
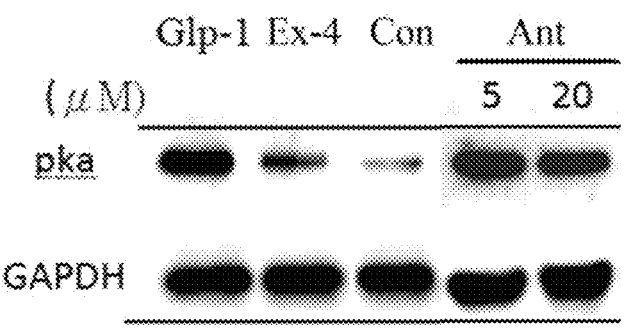
FIG. 4 shows the effects of antroquinonol (Ant) on glucagon like peptide-1 induced PKA protein levels in AR42J cells; wherein the AR42J cells were treated with 1 nM of glucagon-like peptide-1 (Glp-1), 1 nM of exaanid-4 (Ex-4), and various concentrations (5 μM and 20 μM) of antroquinonol (Ant) for 48 h; wherein the levels of protein expression were determined by Western blot, and GAPDH was used as an internal control.

As indicated in FIG. 4, antroquinonol effectively inhibited the DPP4 enzyme activity by enzymatic experiments, subsequently these compounds were used to test whether potentiate glucagon like peptide-1 induced PKA protein level in AR42J cell. It is indicated that glucagon-like peptide-1 (GLP-1) and exendin-4 two hormones with natural compounds were performed to treat cells for measuring the PKA expression (wherein PKA protein level was expressed in antroquinonol).

Example 5 Glucose Uptake Capacity of Antroquinonol

It is known that glucose uptake is through the recruitment of GLUT4 to the plasma membrane (GLUT4 translocation) where these transporters can facilitate glucose uptake. The ability of glucose uptake is determined by the cellular levels, which controlling the amount of the GLUT4 glucose transporter present in the plasma membrane.

5.1 Measurement of GLUT4 Translocation

C2C12 was fully differentiated with DMEM supplemented with 1% FBS and 1% horse serum for 4 days. The cells were washed twice with PBS containing 0.1% BSA and subsequently incubated in PBS with or without the treatment with 185 μM insulin (Ins), 16 mM metformin (Met), or 50, 100, and 150 μM of antroquinonol (Ant) for 55 min (n=5 in each group) respectively, and then placed on ice and immediately fixed with 1% glutaraldehyde in PBS at RT for 10 min. After quenching with 0.1 M glycine in PBS for 10 min, the cells were blocked with PBS containing 5% mouse serum for 30 min. To determine the cell surface GLUT4 content, the cells were then incubated with anti-GLUT4 antibody (Santa Cruz, Calif., USA) diluted to 1 ng/mL in PBS containing 3% mouse serum for 1 h. Next step, the cells were treated with a secondary antibody-horseradish peroxidase (HRP)-conjugated anti-Goat IgG (Jackson ImmunoResearch, Suffolk, UK) diluted 1:300 in PBS containing 3% mouse serum for 1 h. Following a rinsing step with PBS, TMB substrate (BioLegend, Calif., USA) was added and incubated at RT for 30 min, and added 2 N $H_2SO_4$ to stop the reaction. HRP activity was determined by measuring the absorbance at 450 nm with a spectrophotometer (EnSpire 2300 Multilabel Reader, Perkin Elmer, Waltham, Mass., USA).

Figure 5A:
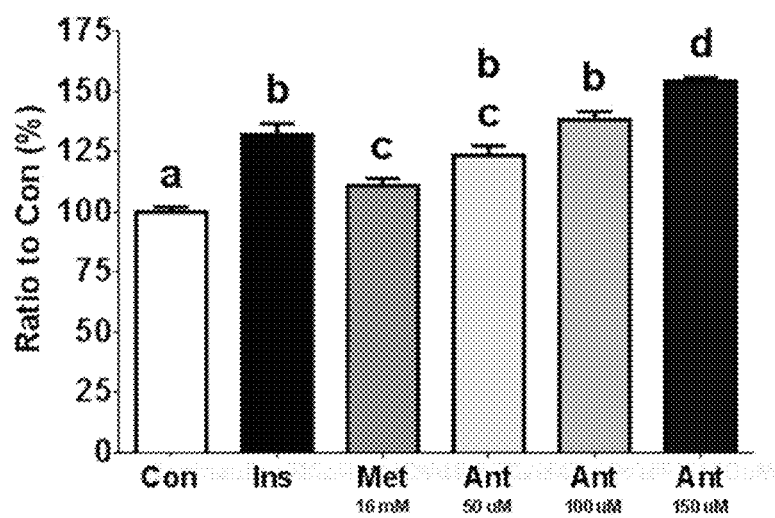
FIGS. 5(A) and 5(B) show the effects of antroquinonol on GLUT4 translocation.

The results are shown in FIG. 5(A), indicating that antroquinonol has a good effect on GLUT4 translocation similar to insulin (Ins), and which is even better than metformin (Met).

Figure 5B:
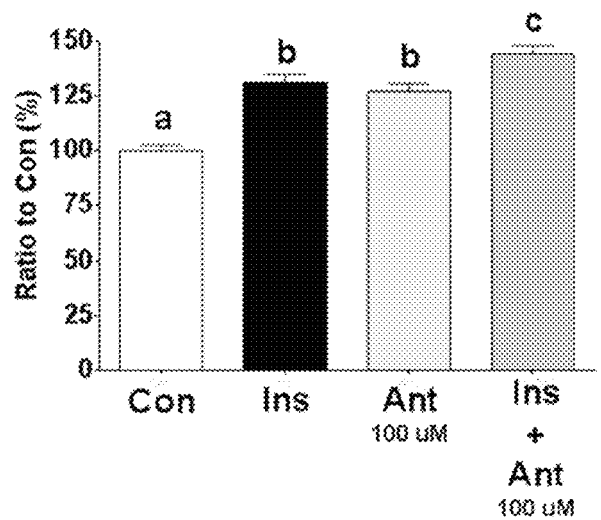

On the other hand, the differentiated C2C12 cells were treated with insulin, antroquinonol, and insulin plus antroquinonol for 40 min (n=5 in each group). The results are shown in FIG. 5(B), indicating that antroquinonol and insulin treated simultaneously provided the synergistic effects.

5.2 Glucose Uptake Assay

The glucose uptake assay was followed previous study (Yamamoto et al., "An enzymatic fluorimetric assay to quantitate 2-deoxyglucose and 2-deoxyglucose-6-phosphate for in vitro and in vivo use." *Analytical Biochemistry* 404(2): 238-240, 2010) with minor modification and the technique generously assistant from Professor Hitoshi Ashida lab (Kobe University, Kobe, Japan). The differentiated L6 myotubes seeding in 96 well microplate were incubated with 100 μL/well of α-MEM with 0.25% BSA in the presence insulin, 5961 (insulin receptor antagonist, a generous gift from Dr. Lauge Schïffer, Novo-Nordisk, Denmark), metformin, and antroquinonol for 30 min. After incubation, the cells were washed twice with KRH. The L6 myotubes were then incubated with KRH buffer containing 1 mM of 2-deoxyglucose (2DG, Sigma-Aldrich, St. Louis, Mo. USA) and 0.1% BSA 60 μL in 5% $CO_2$ at 37° C. for 20 min. After incubation, the cells were washed twice with KRH buffer and then 50 μL of 0.1 N NaOH was added. The microplate was dried by incubated at 85° C. for 90 min. The components in the wells were then neutralized by the addition of 50 μL of 0.1 N HCl and then 50 μL of 50 mM triethanolamine hydrochloride (TEA) buffer (200 mM KCl, 200 mM TEA pH 8.1) was added. Uptake of 2DG into the cells was measured by the enzymatic fluorescence assay. The fluorescence assay buffer was composed by 50 mM TEA buffer, 0.1% BSA, 2.5 mM β-NADP (Wako Pure Chemical, Osaka, Japan), 0.05 unit Diaphorase (Wako), 150 unit *L. mesenteriodes* G6PDH (sigma), and 0.5 mM Resazurin sodium salt (sigma). 10 μL of 2DG sample with 100 μL of fluorescence assay buffer were reacted at 37° C. for 30 min. At the end of the incubation, fluorescence at 570 nm with excitation at 540 nm was measured by spectrophotometer (EnSpire 2300 Multilabel Reader, Perkin Elmer, Waltham, Mass., USA).

Figure 6:
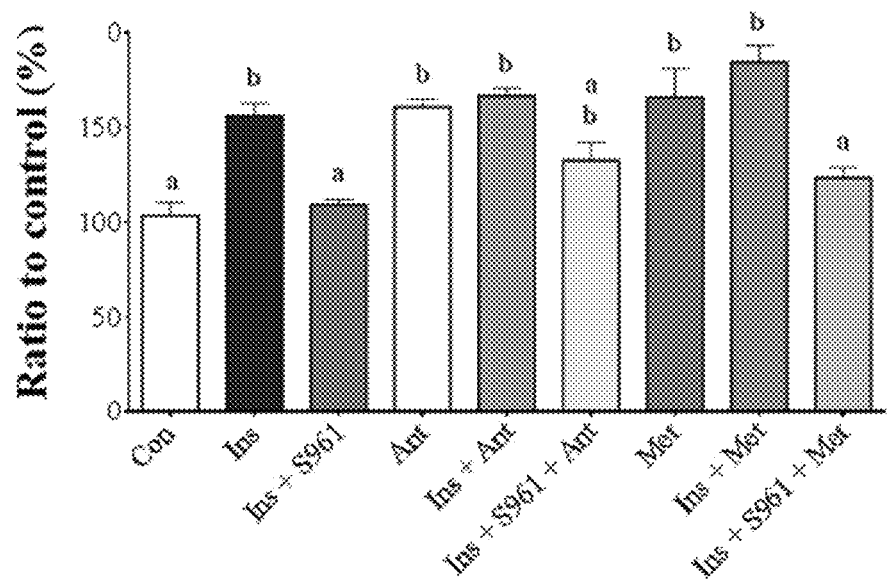
FIG. 6 provides the results of glucose uptake assay for insulin (Ins), metformin (Met) and antroquinonol (Ant); wherein the L6 cells were differentiated and treated with 1 μM of insulin (Ins), 2 mM of metformin (Met), and/or 10 nM of antroquinonol (Ant), and/or 400 nM of 5961 (an antagonist for insulin receptor, used to mimic DM) for 30 min (n=5 in each group); wherein the data were expressed as means with standard errors of mean (mean±SEM), and different letters represent the significant differences (p<0.05) among the various treatments.

As shown in FIG. 6, insulin (Ins), metformin (Met) and antroquinonol (Ant) provided the similar effects on glucose uptake.

In summary, antroquinonol enhanced GLUT4 translocation with dose-dependent manner. Metformin and insulin were administrated as a clinical drug to control glucose uptake. In addition, 100 μM of antroquinonol was equivalent to 16 mM metformin administration with similar profile in this assay (see FIG. 5(A)). When antroquinonol and insulin treated simultaneously, the results showed the synergistic effects (see FIG. 5(B)). It can be concluded that antroquinonol alone possessed the ability of insulin-independent GLUT4 translocation improved in vitro. Antroquinonol provided the effects on glucose uptake similar to insulin and metformin (see FIG. 6).

Example 6 Effect of Glycemic Control In Vivo of Antroquinonol 6.1 Animals Test Animal experiments were approved by the National Dong-Hwa University Animal Ethics Committee and were used according to the "Guide for the Care and Use of Laboratory Animals" of National Dong-Hwa University. C57BL/6 mouse and Imprinting Control Region (ICR) mouse were obtained National Laboratory Animal Center (Taipei, Taiwan) and kept at controlled environmental conditions with room temperature (22±2° C.) and humidity (50±10%). The 12 h light (0600 am-1800 pm) and 12 h dark cycle was maintained throughout the study. Mice had free access to food and water and maintained on a standard laboratory diet (carbohydrates; 60%, proteins; 28%, lipids; 12%, vitamins; 3%).

6.2 Oral Glucose Tolerance Test (OGTT) of Antroquinonol

Mice were employed to this test after fasting 12 h. Mice were treated with D-glucose by oral gavage (2 g/kg, p.o.). At approximately 0, 30, 60, 90, and 120 min, blood was sampled by venipuncture from the tail vein for the determining blood glucose. Blood glucose was immediately determined by the glucose oxidase method using glucose analyzer (Accu-Chek, Roche).

6.3 Short Term Glucose Tolerance Efficacy of Antroquinonol on Insulin Resistance Mice 8 weeks old male C57 BL/6 mice were employed to this test after fasting 12 h. To investigate the effect of natural compounds on the S961 (insulin receptor antagonist, Novo-Nordisk, Denmark) induced hyperglycemia, mice was intraperitoneally injected (i.p.) S961 (50 nmol/kg Bwt) at 15 min prior to oral gavaged (p.o.) with antroquinonol (dissolved in PEG and EtOH, 50 mg/kg Bwt) and D-glucose (2 g/kg Bwt). At approximately 0, 30, 60, 90, and 120 min, blood was sampled by venipuncture from the tail vein for OGTT test.

As shown in FIG. 7(A), antroquinonol had the hypoglycemic efficacy in the condition of insulin resistance through the oral glucose tolerance test (OGTT), similar to Metformin. Further, as shown in FIG. 7(B), (+)-antroquinonol and (−)-antroquinonol both had the hypoglycemic efficacy in the condition of insulin resistance through the oral glucose tolerance test (OGTT).

Example 7 Efficacy of Antroquinonol on Glucose Tolerance in Diet-Induced Obesity (DIO) ICR Mice 7.1 Diet-Induced Obesity (DIO) ICR Mice 8 weeks old ICR male mice were induced with high fat die and 60% fructose water for 10 weeks. The high fat diet comprised 1 kg conventional chow plus 150 g conventional lard (23% total saturated fatty acids and 77% total unsaturated fatty acid, Chinshan oil, Wei Li Foods Co., Changhua, Taiwan). The experimental mice were allotted into 2 groups (1) Group A is Diet induced Glucose intolerance (DIG, n=30) and Group B feeds a normal diet (Con, n=5). After feed high fat diet and 60% fructose water for 10 weeks, ICR male mice were oral gavaged (p.o.) with D-glucose (2 g/kg) after fasting 12 h. At approximately 0, 30, 60, 90, and 120 min, blood was sampled by venipuncture from the tail vein for the determining blood glucose. Blood glucose was immediately determined by the glucose oxidase method using glucose analyzer (Accu-Chek, Roche), when blood sugar was sustained at higher level than 200 mg/dl after 120 min oral glucose that defined high blood sugar.

7.2 Short Term Efficacy of Antroquinonol on Glucose Tolerance of DIO ICR Mice

DIO mice were given 25 mg/kg Bwt of antroquinonol or 20 mg/kg Bwt of Sitagliptin at 15 min prior to oral gavaged (p.o.) with D-glucose (2 g/kg) for glucose tolerance by OGTT test. The results are given in FIG. 8, indicating that antroquinonol provided the effects similar to Sitagliptin.

7.3 Long Term Efficacy of Antroquinonol on Glucose Tolerance of DIO ICR Mice

Antroquinonol (25 mg/kg Bwt) and Sitagliptin (10 mg/kg Bwt) were used to treat DIO mice every other day (q.o.d) for 4 weeks. At the end of long term treatment, mice were performed to measure glucose tolerance by OGTT test. The results are given in FIG. 9, indicating that antroquinonol provided the effects similar to Sitagliptin.

Statistical Analysis

All of the data in these examples were expressed as means±SEM. Statistical comparisons of the results were made using one-way analysis of variance (ANOVA). Means within each column followed by the different letters are significantly different at $p<0.05$ by Tukey's test.

In view of the results of the in vitro and in vivo studies provided above mentioned, it is concluded that antroquinonol is potential for glycemic control via the enhancement of glucose transporter 4 translocation improved glucose uptake, and thus it can be developed as a drug for treating diabetes mellitus, particularly type 2 diabetes mellitus.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

We claim:

1. A method for treating diabetes mellitus in a subject, comprising administering to a subject in need thereof a pharmaceutical composition comprising a pharmaceutically acceptable carrier and a therapeutically effective amount of (−)-antroquinonol, having the formula (IV):

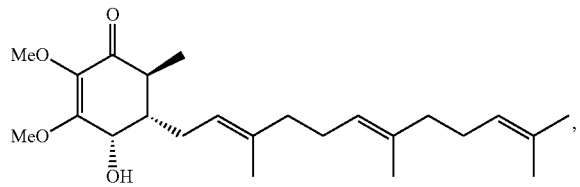

Formula (IV)

wherein Me is methyl.

2. A synthetic compound, which is (−)-antroquinonol having the formula (IV):

Formula (IV)
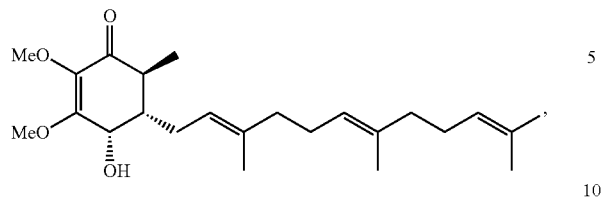
wherein Me is methyl.
3. A pharmaceutical composition for treating diabetes mellitus comprising (−)-antroquinonol having the formula (IV):
Formula (IV)
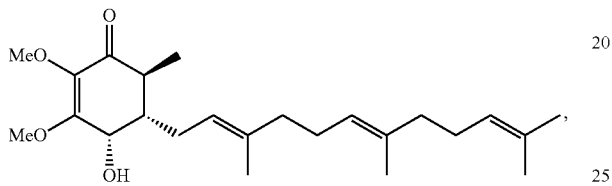
wherein Me is methyl,
and a pharmaceutically acceptable carrier.
4. The pharmaceutical composition for treating diabetes mellitus of claim 3, further comprising insulin or an insulin analogue.
* * * * *